US012758101B2

(12) United States Patent
Graf et al.

(10) Patent No.: US 12,758,101 B2
(45) **Date of Patent: *Oct. 13, 2026**

(54) DETERMINING ANGULAR ORIENTATION FOR IMAGING

(71) Applicant: Ninepoint Medical, Inc., Austin, TX (US)

(72) Inventors: Benedikt Graf, Cambridge, MA (US); Eman Namati, Belmont, MA (US)

(73) Assignee: Ninepoint Medical, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,430

(22) Filed: May 7, 2024

(65) Prior Publication Data

US 2024/0285169 A1 Aug. 29, 2024

Related U.S. Application Data

(63) Continuation of application No. 17/849,962, filed on Jun. 27, 2022, now Pat. No. 12,004,842, which is a continuation of application No. 16/118,517, filed on Aug. 31, 2018, now Pat. No. 11,399,718, which is a continuation of application No. 14/279,567, filed on May 16, 2014, now Pat. No. 10,092,189.

(60) Provisional application No. 61/824,688, filed on May 17, 2013.

(51) Int. Cl.

| | |
|---|---|
| ***A61B 5/00*** | (2006.01) |
| ***A61B 5/06*** | (2006.01) |
| ***G01B 9/02*** | (2022.01) |
| ***G01B 9/02056*** | (2022.01) |
| ***G01B 9/02091*** | (2022.01) |

(52) U.S. Cl.

CPC .......... *A61B 5/0073* (2013.01); *A61B 5/0066* (2013.01); *A61B 5/061* (2013.01); *A61B 5/72* (2013.01); *A61B 5/7257* (2013.01); *G01B 9/02058* (2013.01); *G01B 9/02083* (2013.01); *G01B 9/02089* (2013.01); *G01B 9/02091* (2013.01); *A61B 2576/00* (2013.01); *G01B 2290/70* (2013.01)

(58) Field of Classification Search

CPC ..... A61B 5/0073; A61B 5/0066; A61B 5/061; A61B 5/72; A61B 5/7257; A61B 2576/00; G01B 9/02058; G01B 9/02083; G01B 9/02089; G01B 9/02091; G01B 2290/70

See application file for complete search history.

(56) References Cited

U.S. PATENT DOCUMENTS

| | | | | |
|---|---|---|---|---|
| 10,092,189 B2 * | 10/2018 | Graf | .................... | G01B 9/02089 |
| 11,399,378 B2 * | 7/2022 | Feng | .................... | H04W 16/14 |
| 11,399,718 B2 * | 8/2022 | Graf | .................... | G01B 9/02083 |
| 11,502,633 B2 * | 11/2022 | Elmaanaoui | .............. | H02P 6/22 |

(Continued)

OTHER PUBLICATIONS

Notice of Allowance mailed Feb. 7, 2024, filed in U.S. Appl. No. 17/849,962, pp. 1-4.

(Continued)

*Primary Examiner* — Baisakhi Roy

(57) ABSTRACT

The present disclosure provides an OCT imaging system having a variety of advantages. In particular, the OCT system of the present disclosure may provide a more intuitive interface, more efficient usage of controls, and a greater ability to view OCT imaging data.

8 Claims, 5 Drawing Sheets

800

(56) References Cited

U.S. PATENT DOCUMENTS

| | | | | |
|---|---|---|---|---|
| 12,004,842 | B2* | 6/2024 | Graf | G01B 9/02091 |
| 2006/0072191 | A1* | 4/2006 | Akiyama | G02B 21/0048 359/368 |
| 2006/0133565 | A1* | 6/2006 | Takagi | G01N 23/046 378/20 |
| 2009/0018393 | A1* | 1/2009 | Dick | A61B 5/0066 600/109 |
| 2009/0323076 | A1* | 12/2009 | Li | G01B 9/02063 356/479 |
| 2010/0013946 | A1* | 1/2010 | Amano | H04N 23/75 348/222.1 |
| 2011/0021926 | A1* | 1/2011 | Spencer | A61B 5/0073 600/478 |
| 2012/0101374 | A1* | 4/2012 | Tearney | A61B 5/6852 600/425 |
| 2013/0100455 | A1* | 4/2013 | Tearney | G01B 9/02 356/479 |
| 2013/0148345 | A1* | 6/2013 | Yabe | F21V 9/20 362/231 |
| 2014/0187867 | A1* | 7/2014 | Fukuda | A61B 1/0646 600/181 |
| 2014/0343410 | A1* | 11/2014 | Graf | A61B 5/7257 600/425 |

OTHER PUBLICATIONS

Terminal Disclaimer filed Dec. 12, 2023, filed in U.S. Appl. No. 17/849,962, pp. 1-3.

Terminal Disclaimer approved Dec. 12, 2023, filed in U.S. Appl. No. 17/849,962, p. 1.

Response to Non-Final Office Action dated Feb. 12, 2023, filed in U.S. Appl. No. 17/849,962, pp. 1-6.

Non-Final Office Action mailed Jul. 12, 2023, filed in U.S. Appl. No. 17/849,962, pp. 1-8.

* cited by examiner

OCT System
100

730

720

710

DETERMINING ANGULAR ORIENTATION FOR IMAGING

CROSS REFERENCE TO RELATED APPLICATIONS

This application claims the benefit of (i) U.S. Provisional Application Ser. No. 61/824,688 filed May 17, 2013, entitled "Enhanced Frequency-Domain Optical Coherence Tomography Systems," and (ii) U.S. patent application Ser. Nos. 17/849,962, 16/118,517, and 14/279,567, all of which are incorporated herein by reference in their entireties.

TECHNICAL FIELD

The present disclosure relates to optical imaging systems, in particular optical imaging systems utilizing frequency-domain interferometry.

BACKGROUND

Frequency-domain (or "swept-source") optical coherence tomography (OCT) systems are powerful tools that provide non-invasive, high-resolution images of biological samples at higher acquisition speeds and lower signal-to-noise ratios than time-domain OCT systems. FIG. 1 illustrates an exemplary frequency-domain OCT system 100 at a high level. As shown, the exemplary OCT system includes a wavelength-swept laser source 95 (also referred to herein as a frequency swept source) that provides a laser output spectrum composed of single or multiple longitudinal modes to an input of a coupler 72. The coupler 72 divides the signal fed thereto into the reference arm 80 that terminates in the reference mirror 82 and the sample arm 84 that terminates in the sample 86. The optical signals reflect from the reference mirror 82 and the sample 86 to provide, via the coupler 72, a spectrum of signals that are detected by a photo-detector 88.

Despite the many advantages of frequency-domain OCT, conventional implementations can be difficult to set up and optimize. Additionally, conventional implementations can have differences in measured properties and dimensions from system-to-system. It is with respect to this, that the present disclosure is provided.

DESCRIPTION OF EMBODIMENTS

Figure 1:
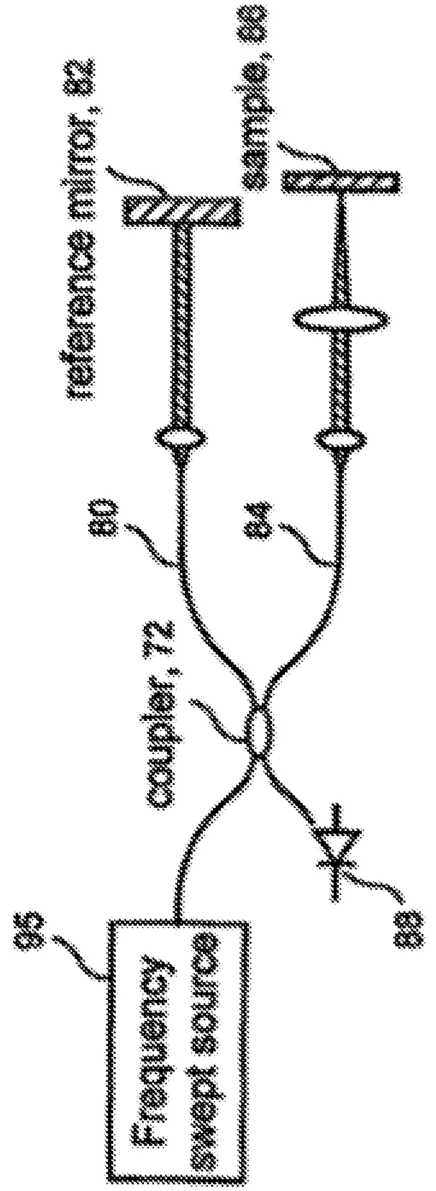
FIG. 1 illustrates a block diagram of a conventional frequency-domain OCT system.
Figure 2:
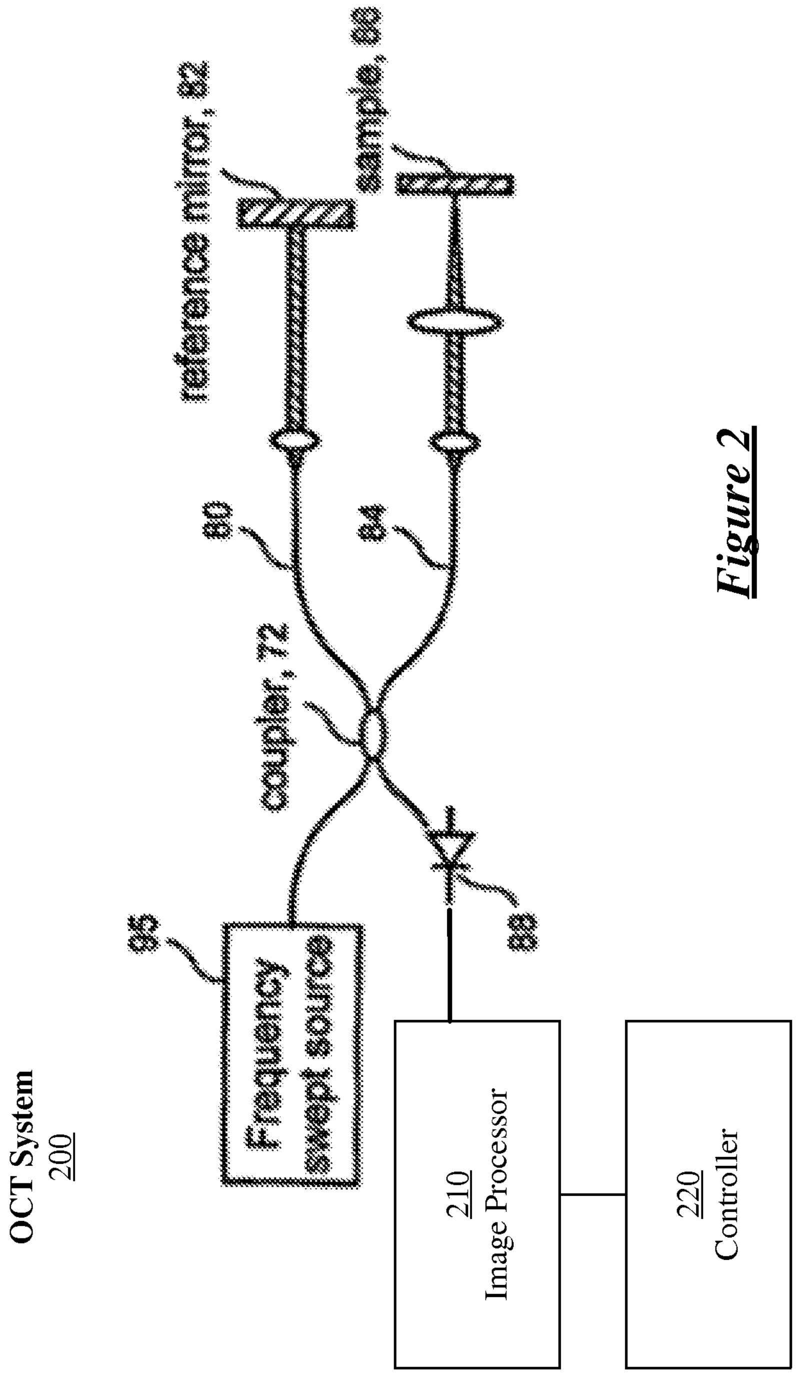
FIG. 2 illustrates a block diagram of a frequency-domain OCT system arranged according to examples of the present disclosure.

In general, the present disclosure provides a variety of apparatuses and methods related to frequency-domain OCT systems. FIG. 2 shows a high level diagram of a frequency-domain OCT system 200, which may be implemented according to various embodiments of the present disclosure. The system 200 includes a wavelength-swept light source 95 that provides a light having an output spectrum composed of single or multiple longitudinal modes. The source 95 provides the light to an input of a coupler 72.

The coupler 72 divides the signal fed thereto into a reference arm 80 and a sample arm 84. The reference arm 80 terminates in the reference mirror 82, also referred to as a reference plane. The sample arm terminates in a sample 86. Optical images reflected from the sample 86 and the reference mirror 82 are received by a photodetector 88 and processed by a signal processor 210.

Additionally, the system 200 includes a controller 220. In general the signal processor 210 may be configured to implement various image processing operations on the images acquired by the system 200 while the controller 220 may be configured to control various aspects of the system 200. This will be described in greater detail below with reference to the example embodiments. It is important to note, that the controller 220 may be operably connected to various components within the system 200. However, these connections are not shown in FIG. 2 for clarity of presentation.

The signal processor 210 may be realized as software, hardware, or some combination thereof. The processor may also include a main memory unit for storing programs and/or data relating to the methods described herein. The memory may include random access memory (RAM), read only memory (ROM), and/or FLASH memory residing on commonly available hardware such as one or more ASICs, FPGAS, electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, or other storage devices.

For embodiments in which the functions of the processor are provided by software, the program may be written in any one of a number of high-level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

Additionally, the controller 220 may be realized as software, hardware, or some combination thereof. The processor may also include a main memory unit for storing programs and/or data relating to the methods described herein. The memory may include random access memory (RAM), read only memory (ROM), and/or FLASH memory residing on commonly available hardware such as one or more ASICs, FPGAS, electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, or other storage devices.

For embodiments in which the functions of the processor are provided by software, the program may be written in any one of a number of high-level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

Other examples and aspects of the OCT system 200 are described in greater detail in U.S. Pat. No. 7,733,497 and U.S. patent application Ser. No. 13/412,787, the disclosures of which are both incorporated by reference herein in their entirety.

It is noted, that although various examples described herein reference the OCT system 200, this is merely done for convenience and clarity and is not intended to be limiting.

In conventional OCT systems, maintaining a consistent angular orientation of the cross-sectional images can be difficult. In particular, because the rotation of the catheter and the acquisition of data are typically not synchronized, the angular position of the image may be different each time a new image acquisition begins. This can manifest as blurring and/or the features in the image changing locations during viewing. Furthermore, conventional OCT systems typically suffer from precession. Precession occurs where the orientation of the image drifts during acquisition, due to, for example, variations in the rotational speed of the catheter.

Figure 3C:
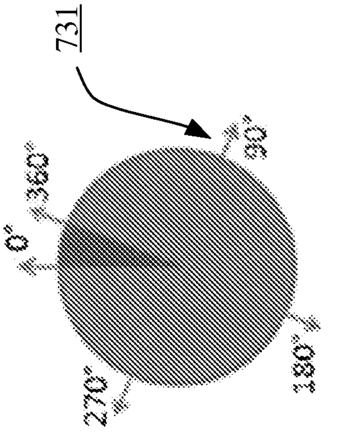
FIGS. 3A-3C illustrate the impact of precession on an PCT image.
Figure 3B:
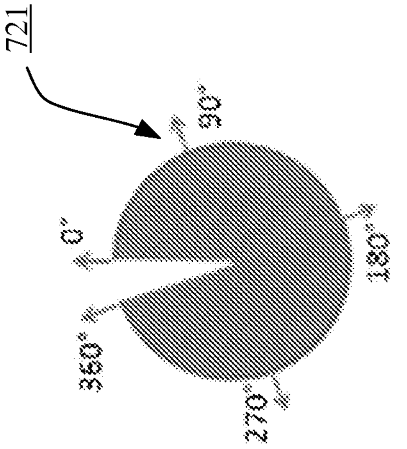
Figure 3A:
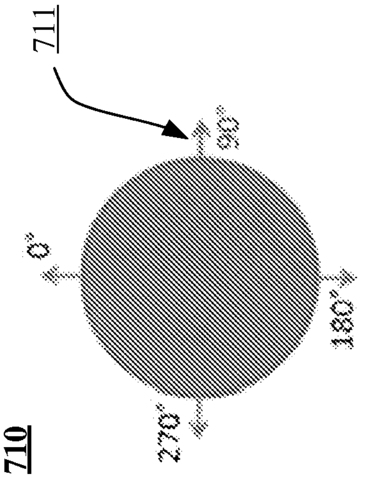

FIGS. 3A-3C illustrate the impact of precession on the orientation of OCT images. In particular, FIG. 3A depicts an acquired OCT frame 710 corresponding to correct rotational speed of the catheter. More specifically, the OCT frame 710 is captured as the catheter completes a single rotation. Accordingly, the angular positioning 711 (e.g., 90 degrees, 180 degrees, 270 degrees, 360 degrees, or the like) will be correctly represented in the frame. FIG. 3B depicts an acquired OCT frame 720 where the rotation of the catheter is too slow. More specifically, as can be seen, the OCT frame 720 is captured before the catheter completes the rotation. As such, the angular positioning 721 (e.g., 90 degrees, 180 degrees, 270 degrees, 360 degrees, or the like) will be incorrectly represented in the frame. In particular, the angular position 721 will be compressed. FIG. 3C depicts an acquired OCT frame 730 where the rotation of the catheter is too fast. More specifically, as can be seen, the OCT frame 730 is captured while the catheter completes more than one full rotation. As such, the angular positioning 731 (e.g., 90 degrees, 180 degrees, 270 degrees, 360 degrees, or the like) will be incorrectly represented in the frame. In particular, the angular position 731 will be stretched.

In either case (e.g., FIGS. 3B-3C) where the angular rotation of the catheter is incorrect, the corresponding OCT image shows incorrect data and the errors accumulate over multiple frames, which can cause rotation of the image orientation (i.e., precession). In addition to constant errors in the rotation velocity (e.g., as depicted in FIGS. 3A-3C), changes in the rotational speed of the catheter may occur during a frame, as such, different parts of the image can be stretched or compressed. This is typically referred to as non-uniform rotational distortion (NURD).

As mentioned previously, encoders may be used to measure and correct for angular velocity deviations caused by the motor. However, the catheter itself may also cause changes in rotation speed, which generally cannot be detected by the encoders. As will be appreciated, variations in the rotational speed may be due to both inherent imperfections in system itself (e.g., the fiber optic rotary junction (FORJ)) as well as NURD.

Embodiments of the present disclosure may be implemented to align the orientation of OCT images using measurements of the catheter's angular orientation. In particular, the angular position of the catheter can be measured and the OCT images aligned accordingly. In some examples, the catheter's angular orientation can be measured using encoders. For example, the system 200 may be implemented with encoders on the motor used to rotate the catheter.

In some examples, the catheter's angular orientation can be inferred by using image processing techniques on the OCT images. In particular, the signal processor 210 may apply image-processing techniques to detect the angular position based on inherent image features present in the OCT images. As another example, the system 200 can be implemented with registration marks in the catheter. As such, the signal processor 210 can detect the angular position based on the registration marks. Correcting image orientation may be achieved either by synchronizing the acquisition of data with rotation of the catheter or by correcting angular distortions in post processing (e.g., using two-dimensional interpolation, or the like.)

Figure 4:
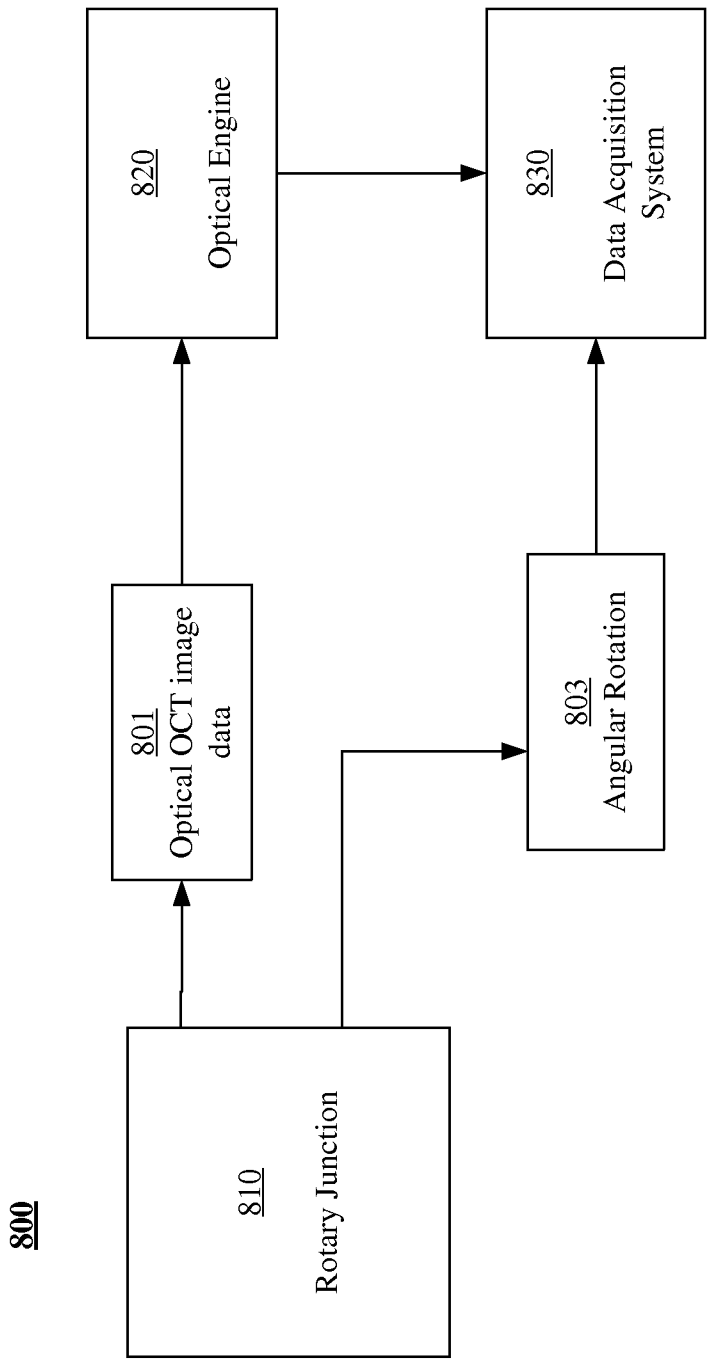
FIG. 4 illustrates a block diagram of a system for adjusting the angular orientation of an image according to some examples of the present disclosure.

FIG. 4 depicts a block diagram of a system 800 that may be implemented to align the orientation of the OCT images as described herein. As depicted, the system 800 includes a rotary junction 810 (e.g., a FORJ, or the like), an optical engine 820 (e.g., the signal processor, or the like) and a data acquisition system 830. It is important to note, that the optical engine 820 and the data acquisition system 830 (DAQ) can be implemented as a single unit or as separate units. Examples are not limited in this context.

In general, OCT image data 801 is transmitted from the rotary junction 810 to the optical engine 820 while a measure of angular rotation 803 (e.g., the angular rotation of the catheter) is transmitted to the DAQ 830. In some examples, the measure of angular rotation 803 corresponds to an electrical signal transmitted from a sensor on the motor used to rotate the catheter. For example, the sensor can indicate the "north" position, the "0 degree" position, or the like. The optical engine 820 receives optical OCT image data 801 from the rotary junction 810 and converts the optical OCT image data 801 to electrical signals, which are communicated to the DAQ 830. Accordingly, the DAQ 830 can align the image data received from the optical engine 820 based on the received measure of angular rotation 803.

Figure 5A:
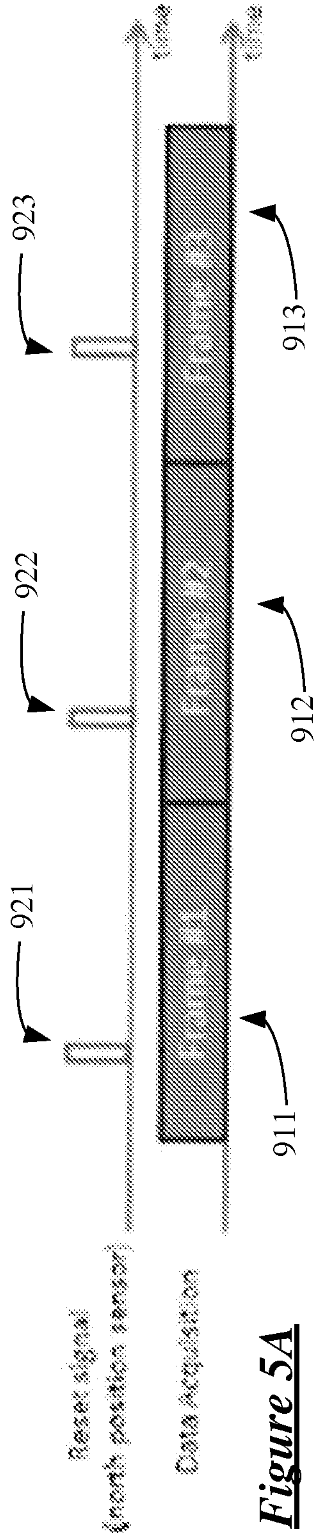
FIGS. 5A-5C illustrate examples of aligning the angular orientation of images arranged according to examples of the present disclosure.
Figure 5B:
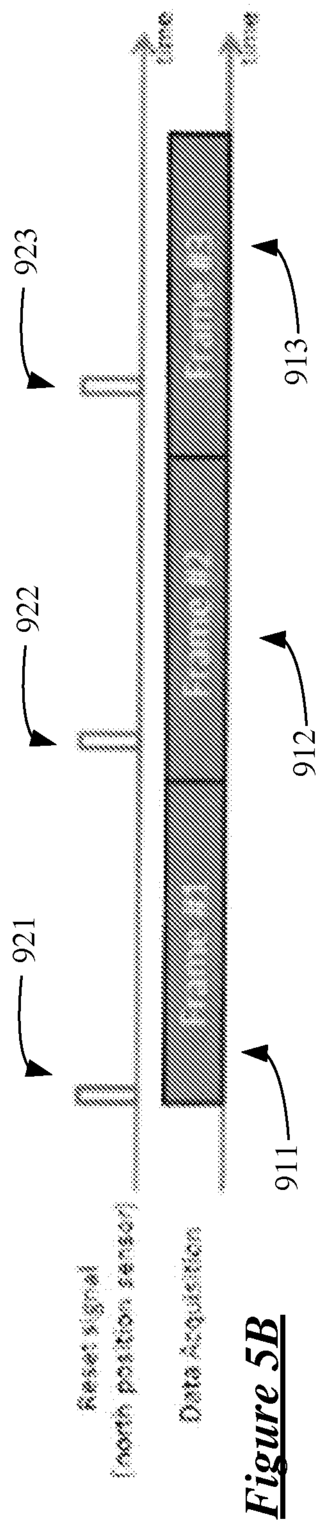
Figure 5C:
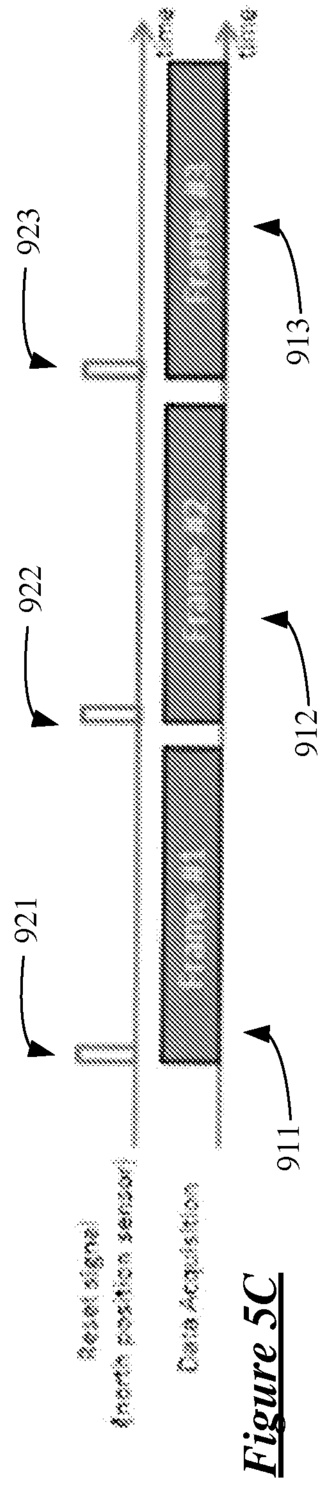

FIGS. 5A-5C illustrate examples of aligning the angular rotation of an acquired frame with the angular rotation (or speed) of the catheter. In general, these figures depict acquired OCT frames 911, 912, and 913 a corresponding rotational position signals 921, 922, and 923. The system 800 is configured to align the OCT data in the frames 911-913 based on the corresponding position signals 921-923. For example, FIG. 5A depicts synchronization of image acquisition for standard OCT acquisition. More specifically, acquisition of the frames 911, 912, and 913 is independent of the timing of the rotational position signals 921, 922, and 923. It is noted, that in this example, acquisition of data starts independent of the orientation of the catheter. More specifically, acquisition of the frame 911 is not synchronized with receipt of the rotational position signal 911. It is noted, that this may result in a different angular image orientation each time an acquisition starts.

FIG. 5B depicts synchronization of the data acquisition with the rotational position signals. In particular, by waiting for the rotational position signals 911 to start the acquisition of the frame 911, a consistent initial image orientation is achieved.

Additionally, the system 800 may be implemented to correct for precession, such as, for example procession due to the rotary junction. FIG. 5C depicts an example where the acquisition of each frame of OCT data is aligned or synchronized with the corresponding rotational position signal. In particular, initiation of acquisition of the frame 911 is synchronized with the corresponding rotational position signal 921. Likewise, initiation of acquisition of the frames 912 and 913 are synchronized with the corresponding rotational position signals 922 and 923, respectively. As such, the orientation of the image will not drift during the acquisition.

As will be appreciated, the catheter itself may also cause changes in rotational speed, which generally cannot be detected by the encoders. These changes may be corrected by using image processing to either track the angular changes as a function of time based on image correlation or by detecting registration marks purposely added to the catheter. One example of tracking angular changes includes using cross-correlation between adjacent segments of the image to measure how rapidly an image changes.

Faster angular rotation results in a lower correlation and slower rotation results in greater correlation. This information may be used to calculate rotational speed. The use of registration marks may include adding features to the catheter sheath or balloon that cause a noticeable change in the image, such as a reduction of intensity. Image processing methods may be used to detect the locations of these features, which then provide an indirect measurement of the angular orientation.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A rotary imaging system for imaging a sample, the system comprising:

means for generating a plurality of image frames of the sample and angular rotational position signals, wherein each angular rotational position signal corresponds to an image frame within a plurality of the image frames and each rotational position signal is generated based on a known position of a rotary junction such that acquisition of each image frame is synchronized to the corresponding known position of the rotary junction;

means, coupled to the means for generating, for receiving the image frames generated by the means for generating;

means, coupled to the means for generating, for receiving the rotational position signals and align an orientation of the image frames based on the angular rotational position signals, wherein synchronizing acquisition comprises synchronizing acquisition of a first one of the plurality of image frames with a first one of the rotational position signals and synchronizing acquisition of a second one of the plurality of image frames with a second one of the rotational position signals.

2. The rotary imaging system of claim 1, wherein (i) the means for generating comprises a fiber optic rotating junction (FORJ) and (ii) the image is acquired using the FORJ, and (iii) the means for receiving is capable of determining a measure of angular rotation corresponding to the image from a rotation speed of the FORJ.

3. The rotary imaging system of claim 1, wherein (i) the means for generating comprises a fiber optic rotating junction (FORJ) and (ii) the image is acquired using the FORJ, the system further comprising:

means for determining a measure of the angular rotation corresponding to the image by at least receiving a position of the FORJ.

4. The rotary imaging system claim 1, wherein the image is acquired using a fiber optic rotating junction (FORJ), and the means for receiving is capable of determining a measure of the angular rotation corresponding to the image from a rotational speed and a position of the FORJ.

5. The rotary imaging system of claim 4, further comprising:

means for determining a rotation speed and the position of the FORJ from a signal received from one or more sensors operably coupled to the FORJ, the signal corresponding to a fixed point of the rotation of the FORJ.

6. The rotary imaging system of claim 1, further comprising:

means for initiating acquisition of the image, wherein to align orientation of the image comprises to synchronize initiating acquisition of each of the images based on respective determined measures of angular rotation.

7. The rotary imaging system of claim 1, wherein the signals comprise optical signals, and the rotary imaging system comprises an optical coherence tomography (OCT) system.

8. The rotary imaging system of claim 7, wherein the OCT system is a frequency-domain OCT system.

* * * * *